(12) United States Patent
Steadman Booker et al.

(10) Patent No.: US 9,955,930 B2
(45) Date of Patent: May 1, 2018

(54) SENSOR DEVICE AND IMAGING SYSTEM FOR DETECTING RADIATION SIGNALS

(71) Applicant: KONINKLIJKE PHILIPS N.V., Eindhoven (NL)

(72) Inventors: Roger Steadman Booker, Aachen (DE); Amir Livne, Zichron Ya'Aqov (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days. days.

(21) Appl. No.: 15/118,911

(22) PCT Filed: Nov. 2, 2015

(86) PCT No.: PCT/EP2015/075363
§ 371 (c)(1),
(2) Date: Aug. 15, 2016

(87) PCT Pub. No.: WO2016/066850
PCT Pub. Date: May 6, 2016

(65) Prior Publication Data
US 2017/0227658 A1 Aug. 10, 2017

(30) Foreign Application Priority Data
Oct. 31, 2014 (EP) .................................... 14191210

(51) Int. Cl.
*A61B 6/03* (2006.01)
*G01T 1/24* (2006.01)
(Continued)

(52) U.S. Cl.
CPC .............. *A61B 6/4241* (2013.01); *A61B 6/03* (2013.01); *A61B 6/4208* (2013.01);
(Continued)

(58) Field of Classification Search
CPC ... A61B 6/4233; A61B 6/4241; A61B 6/4208; G01T 1/24; G01T 1/243
(Continued)

(56) References Cited

U.S. PATENT DOCUMENTS 5,635,718 A * 6/1997 DePuydt ........... H01L 27/14634
250/208.1
6,396,898 B1 * 5/2002 Saito .................... G01N 23/046
378/19
(Continued)

FOREIGN PATENT DOCUMENTS

GB 2332608 6/1999

*Primary Examiner* — Allen C. Ho

(57) ABSTRACT

The present invention relates to a sensor device for detecting radiation signals. To enable high signal integrity and cost efficiency while maintaining the capability of being four-sidedly buttable, the proposed sensor device comprises a sensor array (22) comprising a plurality of detectors (11, 11*a-d*), a sensor element (14) for converting said received radiation signals (74, 74') into a plurality of corresponding electric signals, an interposer element (16, 16*a-d*) extending laterally between a first side (28) and a second side (30), and an integrated circuit element (18, 18*a-d*). The interposer element (16, 16*a-d*) comprises a front surface (24) facing said sensor element (14) and a back surface (26) parallel to said front surface (24), wherein a front contact arrangement (36) is provided on said front surface (24) for directing said electric signals to a back contact arrangement (40) provided on said back surface (26). The integrated circuit element faces said back surface (26) and is electrically connected to said back contact arrangement (40).

15 Claims, 2 Drawing Sheets

(51) Int. Cl.
*A61B 6/00* (2006.01)
*H01L 27/146* (2006.01)

(52) U.S. Cl.
CPC .............. *A61B 6/4233* (2013.01); *G01T 1/24* (2013.01); *G01T 1/243* (2013.01); *H01L 27/14618* (2013.01); *H01L 27/14636* (2013.01); *H01L 27/14658* (2013.01)

(58) Field of Classification Search
USPC .............................. 378/19, 98.8; 250/370.09
See application file for complete search history.

(56) References Cited

U.S. PATENT DOCUMENTS

| | | | |
|---|---|---|---|
| 6,403,964 B1* | 6/2002 | Kyyhkynen | G01T 1/243 250/366 |
| 6,426,991 B1* | 7/2002 | Mattson | A61B 6/032 378/19 |
| 6,510,195 B1* | 1/2003 | Chappo | G01T 1/2018 250/208.1 |
| 6,990,176 B2* | 1/2006 | Sherman | A61B 6/032 250/370.09 |
| 7,136,452 B2* | 11/2006 | Spartiotis | A61B 6/14 378/19 |
| 7,212,604 B2* | 5/2007 | Tkaczyk | G01T 1/2985 378/19 |
| 7,223,981 B1* | 5/2007 | Capote | H01L 27/14634 250/370.13 |
| 7,260,174 B2* | 8/2007 | Hoffman | A61B 6/032 250/363.09 |
| 7,289,336 B2* | 10/2007 | Burdick, Jr. | H05K 1/147 257/428 |
| 7,301,155 B2* | 11/2007 | Tokuda | G01T 1/24 250/370.13 |
| 7,339,176 B2* | 3/2008 | El-Hanany | G01T 1/2928 250/370.09 |
| 7,379,528 B2* | 5/2008 | Mattson | G01N 23/046 250/370.09 |
| 7,450,683 B2 | 11/2008 | Tkaczyk | |
| 7,532,703 B2* | 5/2009 | Du | A61B 6/032 378/116 |
| 7,606,346 B2 | 10/2009 | Tkaczyk | |
| 7,606,347 B2* | 10/2009 | Tkaczyk | A61B 6/032 378/19 |
| 7,613,274 B2* | 11/2009 | Tkaczyk | A61B 6/032 378/19 |
| 7,634,061 B1* | 12/2009 | Tümer | G01T 1/247 378/62 |
| 7,916,836 B2 | 3/2011 | Tkaczyk | |
| 8,304,739 B2* | 11/2012 | Van Veen | G01T 1/24 250/370.08 |
| 8,525,122 B2* | 9/2013 | Chappo | A61B 6/00 250/370.11 |
| 8,548,119 B2* | 10/2013 | Ikhlef | A61B 6/035 378/19 |
| 8,575,558 B2 | 11/2013 | Tkaczyk | |
| 8,659,148 B2* | 2/2014 | Tkaczyk | H01L 27/20 257/722 |
| 8,824,635 B2* | 9/2014 | Tkaczyk | A61B 6/037 250/363.08 |
| 9,012,857 B2* | 4/2015 | Levene | G01T 1/2018 250/370.09 |
| 9,063,240 B2* | 6/2015 | Herrmann | G01T 7/005 |
| 9,069,088 B2* | 6/2015 | Engel | G01T 1/241 |
| 9,207,332 B2* | 12/2015 | Spahn | G01T 1/2928 |
| 9,318,518 B2* | 4/2016 | Hermann | H01L 27/14609 |
| 9,337,233 B1* | 5/2016 | Palit | H01L 27/14663 |
| 9,348,036 B2* | 5/2016 | Yamakawa | G01T 1/24 |
| 9,389,320 B2* | 7/2016 | Ogawa | A61B 6/14 |
| 9,417,339 B2* | 8/2016 | Spahn | G01T 1/247 |
| 9,417,345 B2* | 8/2016 | Reitz | G01T 7/005 |
| 9,519,069 B2* | 12/2016 | Lacey | G01N 23/046 |
| 9,538,107 B2* | 1/2017 | Chappo | A61B 6/032 |
| 9,599,730 B2* | 3/2017 | Spahn | G01T 1/247 |
| 9,613,992 B2* | 4/2017 | Shahar | H01L 27/1446 |
| 9,651,686 B2* | 5/2017 | Lee | G01T 1/247 |
| 9,753,157 B2* | 9/2017 | Steadman Booker | G01T 1/244 |
| 9,761,631 B2* | 9/2017 | Fujita | H01L 27/148 |
| 2010/0327173 A1 | 12/2010 | Woychik | |
| 2013/0049151 A1 | 2/2013 | Lobastov | |

* cited by examiner

SENSOR DEVICE AND IMAGING SYSTEM FOR DETECTING RADIATION SIGNALS

CROSS REFERENCE TO RELATED APPLICATIONS

This application is the U.S. National Phase application under 35 U.S.C. § 371 of International Application No. PCT/EP2015/075363, filed Nov. 2, 2015, published as WO 2016/066850 on May. 6, 2016, which claims the benefit of European Patent Application Number 14191210.5 filed Oct. 31, 2014. These applications are hereby incorporated by reference herein.

FIELD OF THE INVENTION

The present invention relates to a sensor device and an imaging system for detecting radiation signals. It finds application in imaging technologies such as Computer Tomography, in particular Spectral Computer Tomography based on direct conversion sensors.

BACKGROUND OF THE INVENTION

Imaging technologies are widely used to study structures of materials in order to gain information about the materials' properties. In medical imaging, various imaging techniques are used for imaging structures of a subject. In particular, Computer Tomography (CT), Spectral CT, Positron Emission Tomography (PET), Single Photon Emission Computer Tomography (SPECT) are capable of imaging internal structures of a patient in a non-invasive manner.

In the afore-mentioned imaging techniques, particularly in CT and Spectral CT, the subject is irradiated by radiation signals, in particular X-rays, emitted by a radiation source, wherein the subject is irradiated in a plurality of directions. The radiation signals are transmitted through the irradiated subject, in which the radiation signals are partially absorbed and/or scattered. The transmitted radiation signals are subsequently detected by a sensor device, which is positioned on the opposite side of the radiation source with respect to the irradiated subject.

Depending on the specific imaging technique, the radiation signals may be photons of a specific wavelength or a plurality of wavelengths of a specific electromagnetic spectrum. For instance, X-ray-based imaging techniques including CT, mammography and fluoroscopy typically utilize an X-ray radiation source that emits X-rays, wherein the sensor device is configured to detect the X-rays transmitted through the subject. PET utilizes positrons, while SPECT utilizes gamma rays.

In order that the radiation signals or photons can be processed electronically, the sensor device is configured to convert the radiation signals received by the sensor device into corresponding electric signals that are processed by and/or directed to one or more electronic entities, such as an integrated circuit (IC) element, which enable and/or assist the generating of medical images.

It is desirable to obtain medical images which reflect the information about the irradiated subjects as completely as possible. For this purpose, photons transmitted through the irradiated subject in various directions need to be detected, counted and possibly discriminated by energy. (e.g. for Spectral CT). Furthermore, CT systems must provide a large area coverage for clinically relevant diagnosis. In addition, it is also desirable to obtain medical images with high image resolution, so that structural details with low dimensions are detectable. The sensor device comprises a plurality of detectors which form at least one sensor array. In particular, the detectors are arranged so that they are four-sidedly buttable, i.e. the detectors are placed adjacent to each other in various planar directions. In this way a CT sensor device can be built to offer sufficient coverage, i.e. being able to image a significant portion of the body (e.g. heart) in one single rotation.

Numerous sensor devices are known which provide the four-sided buttability. However, the sensor devices known in the field of imaging technologies are limited in signal integrity and cost efficiency.

U.S. Pat. No. 8,575,558 B2 discloses a detector array comprising a plurality of tileable sensor stacks arranged on a first side of a substrate to form a planar detector array, wherein each of the plurality of tileable sensor stacks comprises a detector, an integrated circuit and an interposer element, wherein the interposer element is disposed between the detector and the integrated circuit and configured to operationally couple the detector to the integrated circuit.

US 2010/327173 A1 discloses an integrated direct conversion detector module with a direct conversion crystal with an anode and cathode on opposite sides thereof, as well as an integrated circuit in electrical communication with the direct conversion crystal. A redistribution layer is deposited on the anode layer, which is configured to adapt a pad array layout of the direct conversion crystal to a predetermined lead pattern.

SUMMARY OF THE INVENTION

It is an object of the present invention to provide a sensor device and an imaging system for detecting radiation signals of a subject which enable high signal integrity and cost efficiency while maintaining the capability of being four-sidedly buttable.

In a first aspect of the present invention a sensor device for detecting radiation signals is presented that comprises a sensor array comprising a plurality of detectors, each detector comprising a receiver surface for receiving a plurality of radiation signals transmitted through or emanating from a subject, a sensor element for converting the received radiation signals into a plurality of corresponding electric signals, an interposer element extending laterally between a first side and a second side, the an interposer element comprising a front surface facing the sensor element and a back surface parallel to said front surface, wherein a front contact arrangement is provided on the front surface for directing the electric signals to a back contact arrangement provided on the back surface, and an integrated circuit element facing the back surface and electrically connected to the back contact arrangement, the integrated circuit element comprising a circuit portion extending laterally over the back surface on the second side, the front surface extending laterally over the back surface on the first side by an extrusion comprising an extrusion surface, the circuit portion of a first detector of the sensor array overlapping vertically with and being vertically spaced from the extrusion surface of a second detector adjacent to the first detector.

In a second aspect of the present invention an imaging system for detecting radiation signals of a subject is presented that comprises a radiation source for generating a plurality of radiation signals, radiation directing means for directing the generated radiation signals to the subject and a sensor device disclosed herein for detecting the directed radiation signals emanating from the subject.

Preferred embodiments of the invention are defined in the dependent claims. It shall be understood that the claimed imaging system has similar and/or identical preferred embodiments as the claimed sensor device and as defined in the dependent claims.

Radiation signals generated by a radiation source are transmitted through the subject and received by the receiver surface. Subsequently, the received radiation signals are converted by the sensor element into corresponding electric signals, which are later processed to the integrated circuit element via the interposer element. A function of the interposer element is to mechanically support the sensor element so that the detector is realized with high structural stability. In particular, the detectors are aligned to form the sensor array while unwanted mismatches, gaps and/or offsets between adjacent detectors are avoided.

Additionally, the front contact arrangement and the back contact arrangement enable to direct or route the electric signals obtained by converting the received radiation signals in a desired way. In particular, the front and back contact arrangements possess high compatibility with the integrated circuit element, in particular with an application specific integrated circuit (ASIC). The integrated circuit element, in particular the ASIC, is configured to integrate the charge and forms a pulse whose height is proportional to the energy of the impinging radiation signal, e.g. photon.

The interposer element according to the present invention comprises an extrusion, by which the front surface of the interposer element extends over the back surface on one of the two lateral sides of the interposer element. In this way, the detectors can be staggered into a sensor array, thereby enabling four-sided tileability. This leads advantageously to a large area coverage of the sensor device by being capable of placing detectors adjacent to each other in all planer directions.

Since the front surface and the back surface of the interpose element are parallel to each other, the fabrication of the interposer element is particularly easy so that the sensor device is realized with high cost efficiency. Moreover, unwanted strain effects which would arise from two non-parallel surfaces are significantly reduced or even avoided. Advantageously, there is no need to compensate such unwanted strain effects, for instance by adding an additional compensation element between the back surface of the interposer and the integrated circuit element.

The vertical overlap between the circuit portion and the extrusion surface enables a recess between adjacent detectors which allows to dispose interconnections between an integrated circuit element, in particular an ASIC, and an electronic entity such as a substrate. The possibility to process input/output (I/O) and/or power signals outside of the interposer element is thus provided, which advantageously allows to separate the I/O and/or power signals from the routing signals within the interposer element. In this way, unwanted interferences between pixel signals directed within the interposer element and the I/O and/or power signals are easily avoided, leading to high quality pixel signals. In addition, the interposer element may be realized with reduced complexity.

The "radiation signals" may comprise photons of one or more wavelengths, such as X-ray, gamma ray, and/or positrons. The "electric signals" may comprise charge signals and/or current signals. It is understood that the first detector and the second detector refer to any two adjacent detectors of the sensor array. The terms "vertical" and "lateral" are with respect to the plane in which the front surface or the back surface of the interposer element resides or a plane parallel to the front or back surface of the interposer element.

In a preferable embodiment, the extrusion surface is arranged between the front surface and the back surface. In this way, a recess is formed between the extrusion surface and the back surface of the interposer element. This allows to dispose interconnections between the integrated circuit element of an adjacent detector and an electronic entity, e.g. a substrate in a particularly easy manner. The functionality and cost efficiency are advantageously increased.

In another preferable embodiment, the extrusion surface comprises a surface portion parallel to the front surface. Such an extrusion surface reduces inhomogeneity effects such as strain effects within the extrusion. Furthermore, such an extrusion surface can be easily fabricated. Advantageously, functionality and cost efficiency of the sensor device are increased.

In a further preferable embodiment, the first side of the interposer element comprises an upper side surface connecting the front surface with the extrusion surface, and/or a lower side surface connecting the back surface with the extrusion surface, at least one of the upper side surface and the lower side surface being perpendicular to the front surface. This increases the structural homogeneity and thus mechanical stability of the interposer element while enabling easy fabrication leading to increased cost efficiency.

In a further preferable embodiment, the second side of the interposer element is perpendicular to the front surface. This enables to reduce strain effects on the second side of the interposer element leading to better structural and electronic properties of the interposer element.

In a further preferable embodiment, the detector further comprises a substrate element electrically connected to the integrated circuit element, in particular to the circuit portion. This enables to direct signals, in particular I/O and/or power signals, between the integrated circuit element and the substrate element. Advantageously, the I/O and/or power signals are kept outside of the interposer element, thus reducing or even avoiding their interferences with the electric signals, in particular pixel signals, directed by the interposer element.

Preferably, the substrate element is configured to extend laterally over the circuit portion. This enables to direct the afore-mentioned I/O and/or power signals from the integrated circuit element to the substrate element using a directing path outside of the integrated circuit element, thereby advantageously reducing unwanted signal interferences.

Further preferably, the substrate element is electrically connected to a contact pad provided on the circuit portion by a wire bond. The wire bond (WB) technique is an established technique for fabricating electric interconnections, in particular in low dimensional systems. Advantageously, the application of WB increases the fabrication efficiency and the reliability of the interconnections between the integrated circuit element and the substrate element.

In a further preferable embodiment, the detector further comprises a flexible substrate. The flexible substrate is an established technique for mounting electronic devices. The flexible substrate is highly flexible and can be realized in various desired shapes leading to easy fabrication and higher signal integrity. The flexible substrate may comprise one or more materials of polyamide, PEEK and transparent conductive polyester. In particular, the flexible substrate may be formed as Printed Circuit Boards (PCB). Preferably, the flexible substrate is connected to the integrated circuit element only for directing the I/O and/or power signals. Further preferably, the flexible substrate may extend over the whole surface of the interposer element and/or provided by the two lowermost layers of the interposer element.

In a further preferable embodiment, the integrated circuit element of the first detector is laterally spaced from the integrated circuit element of the second detector. This enables a gap between the integrated circuit elements of adjacent detectors, which advantageously allows to dispose interconnections between the integrated circuit element and an electronic entity, e.g. the afore-mentioned substrate element.

In a further preferable embodiment, the front contact arrangement comprises a plurality of front contact pads, wherein the back contact arrangement comprises a plurality of back contact pads, wherein each of the front contact pads is configured to direct one of the electric signals to a corresponding one of the back contact pads. This allows to direct each single electric signal, in particular pixel signal, through the interposer element with high reliability. Advantageously, the pixel signals which are used for generating images, in particular medical images, can be obtained with signal integrity.

Preferably, each of the front contact pads is provided with a first lateral dimension and each of the back contact pads is provided with a second lateral dimension, the first lateral dimension being larger than the second lateral dimension. This enables to provide a region of a sufficient size, in particular an area, within the integrated circuit element in order to direct the I/O and/or power signals into the integrated circuit element and/or out of the integrated circuit element. In addition, this is advantageous for the tileability of the sensor device.

Further preferably, the quantity of the front contact pads is the same as the quantity of the back contact pads. This enables low-noise signal routing within the interposer element.

In a further preferable embodiment, the interposer element is formed using pressed layers, in particular pressed polyamide layers. This enables easy fabrication of the interposer element with high precision, in particular regarding thickness and cross section.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
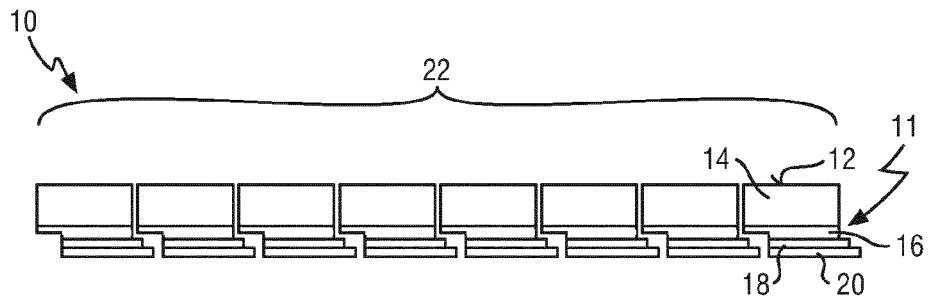
FIG. 1 shows a schematic representation of a sensor array comprising a plurality of detectors according to an embodiment.

FIG. 1 shows a schematic representation of a sensor device 10 for detecting radiation signals of a subject, comprising a plurality of detectors 11. Each detector 11 comprises a receiver surface 12, a sensor element 14, an interposer element 16 and an integrated circuit element 18. Preferably, each detector 11 further comprises a substrate element 20. The plurality of detectors 11 are arranged to form a sensor array 22, wherein the individual detectors 11 are aligned so that the individual receiver surfaces 12 are arranged on the same side of the sensor array 22. The sensor array 22 comprises eight detectors 11 which are arranged lineally in the embodiment shown in FIG. 1. In another embodiment, the detectors 11 are arranged at least partially along a curvature. In general, the number of the detectors 10 may be larger or smaller than eight.

FIG. 2a shows the detector 11 in more detail. The receiver surface 12 is preferably formed as a top surface of the sensor element 14. The receiving surface 12 comprises preferably top electrodes or cathodes of the sensor element 14, which additionally comprises back electrodes or anodes on it bottom surface connecting the interposer element 16. Between the cathodes and the anodes the sensor element 14 comprises a bulk made of a material suitable for direct conversion radiation sensing such as cadmium telluride (CdTe), cadmium zinc telluride (CdZnTe) gallium arsenide (GaAs), mercury iodide ($HgI_2$), etc. Preferably, the sensor element 14 is configured to convert the received radiation signals directly into corresponding electric signals such as charges or current signals. Further preferably, the sensor element 14 is configured to enable a conversion process by creating an electron-hole pair after receiving a single photon, wherein the electron and/or the hole of the electron-hole pair contributes to the electric signal converted from the radiation signal being the photon. Advantageously, such a sensor element 14 possesses high conversion efficiency.

The interposer element 16 comprises a front surface 24 and a back surface 26, wherein the front surface 24 is parallel to the back surface 26. The interposer element 16 is disposed between the sensor element 14 and the integrated circuit element 18, while the front surface 24 of the interposer element 16 faces the sensor element 14 and the back surface 26 of the interposer element 16 faces the integrated circuit element 18. The interposer element 16 extends laterally from a first side 28 to a second side 30 opposite to the first side 28. The front surface 24 extends laterally over the back surface 26 on the first side 28 by an extrusion 32. The extrusion 32 extends vertically from the front surface 24 to an extrusion surface 34.

The integrated circuit element 18 is arranged between the back surface 26 of the interposer element 16 and the substrate element 20. The integrated circuit element 18 extends laterally from the same height of an edge of the back surface 26 on the first side 28. Further, the integrated circuit element 18 comprises a circuit section 62 extending laterally over the back surface 26 of the interposer element 16 on the second side 30. The integrated circuit element 18 is preferably an Application Specific Integrated Circuit (ASIC), providing high compatibility and reliability of signal processing, leading advantageously to increased signal integrity of the detector 11.

In the embodiment shown in FIG. 2a, the extrusion surface 34 is arranged between the front surface 24 and the back surface 26 and is parallel to the front and back surfaces 24, 26. In this way, the interposer element 16 has a smaller thickness on the first side 28 than on the second side 30. In another embodiment, the interposer element 16 has a larger thickness on the first side 28 than on the second side 30, wherein the extrusion surface 34 extends vertically over the back surface 26 in direction to the integrated circuit element 18.

The first side 28 of the interposer element 16 comprises an upper side surface 28*a* and a lower side surface 28*b*, wherein the upper side surface 28*a* connects the front surface 24 with the extrusion surface 34 and the lower side surface 28*b* connects the back surface 26 with the extrusion surface 34. In the embodiment shown in FIG. 2, both the upper side surface 28*a* and the lower side surface 28*b* are perpendicular to the front surface 24 and the back surface 26. In addition, the second side 30 is also perpendicular to the front surface 24 and the back surface 26. At least one of the upper side surface 28*a*, the lower side surface 28*b* and the second side 30 can be non-perpendicular to the front surface 24 and the back surface 26, as shown in detail in FIG. 3.

As shown in FIG. 2*a*, a front contact arrangement 36 is provided on the front surface 24 of the interposer element 16 comprising a plurality of front contact pads 38. The front contact pads 38 are arranged so that adjacent contact pads 38 are laterally spaced from each other. The front contact pads 38 are configured to receive the electric signals converted from the radiation signals by the sensor element 14. Furthermore, the front contact pads 38 are configured to direct or route the electric signals through the interposer element 16 to a back contact arrangement 40 provided on the back surface 26 of the interposer element 16. The back contact arrangement 40 comprises a plurality of back contact pads 42, which are arranged so that adjacent back contact pads 42 are laterally spaced from each other. It is understood that the quantity of the front contact pads 38 and the back contact pads 42 may vary in different embodiments of the sensor device 10.

The back contact pads 42 are configured to direct the electric signals routed through the interposer element 16 further to the integrated circuit element 18. Every electric signal is routed by one of the front contact pads 38 via the interposer element 16 to a corresponding one of the back contact pads 42.

The front contact pads 38 are provided with a first lateral dimension 48 and the back contact pads 42 are provided with a second lateral dimension 50. Preferably, the first lateral dimension 48 is larger than the second lateral dimension 50. Further preferably, the quantity of the back contact pads 42 is the same as the quantity of the front contact pads 38.

As shown in FIG. 2*b*, every front contact pad 38 and its corresponding back contact pad 42 are connected by a routing path 44*a*, 44*b*, as shown in FIG. 2*b*. Each routing path 44*a*, 44*b* connects a pair of contact pads comprising a front contact pad 38*a*, 38*b* and a corresponding back contact pad 42*a*, 42*b*. Each routing path 44*a*, 44*b* as shown in FIG. 2*b* comprises one or more vertical routing sections and one or more lateral routing sections. In general, the routing path may comprise one or more vertical routing sections, while it may be extended by one or more lateral routing sections. In a preferable embodiment, the vertical routing sections are realized as vias which are compatible to any interposer technology such as based on polyimide, ceramic, FR4, etc.

Each front contact pad 38*a*, 38*b* is configured to route an electric signal corresponding to an image element, such as a pixel, of an image generated by processing the pixel signals to one or more image generation means (not shown). The pixel of the sensor device 10, or device pixel, is defined by the electrodes of the sensor element, wherein each electrode is connected to one of the front contact pads 38*a*, 38*b*. Hence, each front contact pad 38 corresponds to a sensor pixel. The electrical signals directed by the front contact pads 38 are also known as pixel signals and the first lateral dimension 48 is known as pixel pitch of the sensor element 14, or sensor pixel pitch. Generally, the device pixel of the sensor device 10 may comprise a larger lateral size than the front contact pad. For instance, the lateral size of the device pixel may be 300 µm, while the lateral size of the front contact pad 38, i.e. the first lateral dimension 48, may be 100 µm.

Each back pad 42*a*, 42*b* is configured to direct the electric signal routed through the interposer element 16 further to the integrated circuit element 18, where the electric signal will be processed. Each back contact pad 42 corresponds to a circuit pixel and the second lateral dimension 50 may be referred to as circuit pixel pitch. By configuring the first and the second lateral dimensions 48, 50 to have different sizes, the detector 11 is provided with different sensor and circuit pixel pitches.

As shown in FIG. 2*b*, the interposer element 16 comprises a plurality of interposer layers 46, 46' stacked vertically on top of each other. Both routing paths 44*a*, 44*b* are configured to route the electric signal from the front contact pads 38*a*, 38*b* first through a plurality of upper interposer layers 46 beginning from the front surface 24 before the electric signal is routed vertically through a plurality of lower interposer layers 46' arranged more deeply than the upper interposer layers 46 and subsequently to the corresponding back contact pads 42*a*, 42*b*. In FIG. 2*b*, the lateral routing sections of the routing paths 44*a*, 44*b* extend along the interfaces between adjacent layers 46, 46'. In general, the routing paths from the sensor pixels to the circuit pixels may have any track required for routing all pixel signals, wherein the routing paths 44*a*, 44*b* may extend within one layer 46, 46'. In particular, each routing path may extend laterally and vertically, thereby bridging the extrusion 32 within the upper interposer layers 46. In an embodiment, the length of the routing paths decreases from the first side 28 towards the second side 30 of the interposer element 30. On the second side, the connection of the sensor pixel to the circuit pixel is preferably 1:1. The longest routing is given by the need to route the leftmost sensor pixels on the first side 28 to the leftmost circuit pixels on the first side 28 in the representation shown in FIG. 2*b*.

Depending on the actual design rules for a given technology, it may be necessary to resort to a plurality of layers in order to allow routing all electric signals. Hence, the interposer element 16 is preferably made of two or more layers, wherein the minimum being two forming the top and the bottom layer. Each layer 46, 46' is used for lateral routing of the electric signals, thus accommodating the lateral routing sections. The vertical routing of the electric signals are facilitated preferably by vias, such as metal-filled holes.

The front contact pads 38 and/or the back contact pads 42 may in general be formed with different lateral dimensions. In particular, the integrated circuit element 18 has a smaller lateral dimension than the sensor element 14, which enables the I/O and/or power signals to be directed out of the integrated circuit element 18 and/or the detector 11 within the total area of the detector 11. Advantageously, any two detectors 11 can be easily arranged adjacent to each other to enable the four-sided tileability of the sensor device 10. In the preferable embodiment where the front and the back contact pads 38, 42 are provided with the same quantity, the first lateral dimension 48 is larger than the second lateral dimension 50.

The front and the back contact pad 38, 42 may comprise a conductive material such as metal and/or semiconductor. The interposer elements 16 may comprise a semiconductor material and/or a polymeric material. In particular, the interpose elements 16 may be formed using pressed layers of polyamide, polyimide, ceramic, glass, FR4 and/or silicon. The number of interposer layers 46, 46' is 6 in the embodiments shown in FIG. 2b. In general, this number may be different from 6. The number of layers is a trade off between the number of signals, the difference in pitch and the technology. For instance, in the case ceramic is used as pressed layers, the pixel signals can be routed in fewer layers than if FR4 is used, while the routing feature sizes such as width and spacing maybe better resolved. In a preferable embodiment, the lateral routing sections comprise a length of about 6 mm, while the present application is not restricted to this length. In another preferable embodiment, the integrated circuit element 18 comprises an area covered by one or more contact pads used for directing I/O and/or power signals, wherein the lateral dimension of the area is preferably but not restricted to 4-6 mm. Further preferably, the integrated circuit element 18 comprises an ASIC, wherein the lateral dimension of the ASIC is 4-6 mm smaller than that of the interposer element 16 and/or the sensor element 14. In another preferable embodiment, the lateral dimension of the extrusion 32 of the interposer 16 is, but not restricted to, 4-6 mm.

FIGS. 3a and 3b show the interposer element 16 of FIGS. 2a and 2b. In addition, several alternative forms are shown for the extrusion 32 using dashed lines. In FIG. 3a, a first alternative embodiment of the extrusion 32 comprises an extrusion surface 52 which is formed as an inclined surface connecting the front surface 24 and a back surface 26 on a first side 28, wherein the extrusion surface 52 is provided by the first side 28. In another embodiment, the extrusion 32 comprises an extrusion surface 54 which is formed as a devious surface connecting the front surface 24 and the back surface 26 on a first side 28, wherein the extrusion surface 54 is provided by the first side 28.

In the interposer element 16 shown in FIG. 3b, an upper side surface 56a connecting the extrusion surface 34' and the front surface 24 is formed as an inclined surface with respect to the front surface 24. A lower side surface 56b, 56b' connecting the extrusion surface 34' and the back surface 26 is formed as an inclined surface with respect to the back surface 26, wherein the angle 58 between the lower side surface 56b, 56b' and the back surface 26 may be smaller or larger than 90°. It is understood that the angle between the upper side surface 56a and the front surface 24 may be smaller or larger than 90°. The extrusion surface 34' may be parallel to the front and back surfaces 24, 26. In another embodiment, the extrusion surface 34' is formed as an inclined surface with respect to the front and back surfaces 24, 26.

Figure 2:
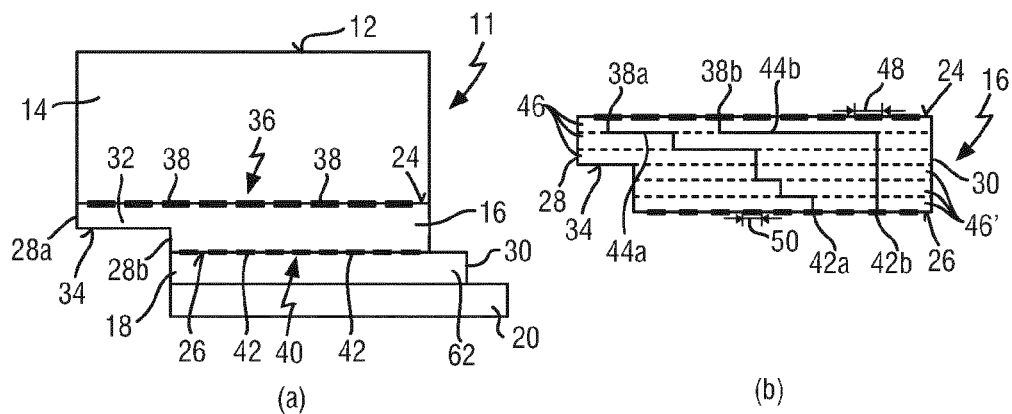
FIGS. 2a and 2b show a schematic representation of one of the detectors in FIG. 1.
Figure 3:
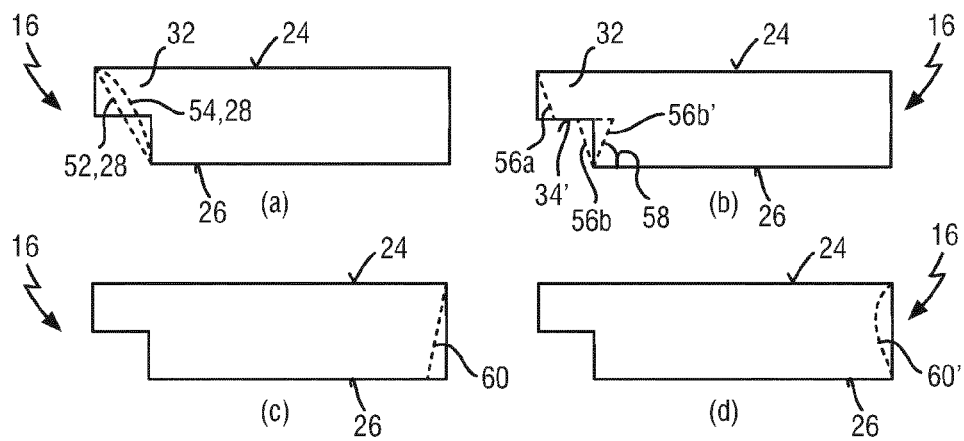
FIGS. 3a-d show a schematic representation of the interposer element of the detector in FIG. 2.

FIGS. 3c and 3d show again the interposer element 16 of FIG. 2, wherein two additional embodiments for the second side 30 are shown by dashed lines. In the embodiment of FIG. 3c, a second side 60 is formed as an inclined surface with respect to the front and back surfaces 24, 26. It is understood that the angle between the second surface 60 and the front surface 24 may be smaller or larger than 90°. In the embodiment of FIG. 3d, a second side 60' is formed as a devious surface, which enables a recess compared to the embodiment shown in FIG. 2. It is understood that the second surface 60' may also be configured to extend laterally over the front and back surfaces 24, 26.

Figure 4:
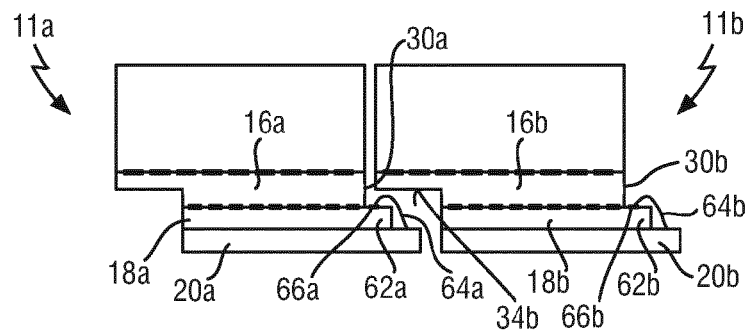
FIG. 4 shows a schematic representation of two adjacent detectors in FIG. 1.

FIG. 4 shows two adjacent detectors 11a, 11b from the sensor array 22 of FIG. 1. The integrated circuit elements 18a, 18b comprise each a circuit section 62a, 62b (for example, a portion of a circuit section 62) which extend laterally over the second side 30a, 30b (for example, a surface) of the interposer element 16a, 16b. The circuit section 62a of the first detector 11a is configured to vertically overlap with the extrusion surface 34b of the second detector 11b. The lateral dimension of the circuit sections 62a, 62b is preferably, but not restricted to, 4-6 mm. In addition, the circuit section 62a of the first detector 11a is vertically spaced from the extrusion surface 34b of the second detector 11b. This allows the first detector 11a and the second detectors 11b to be staggered, enabling four-sided tileability of the sensor array 22. Further, this allows to dispose interconnections between the circuit section 62a and the substrate element 20a of the first detector 11a.

In the embodiment shown in FIG. 4, the substrate element 20a, 20b of the first and the second detectors 11a, 10b are configured to extend laterally over the integrated circuit element 18a, 18b, respectively. In addition, a wire bond 64a, 64b is provided to connect the portion of the substrate element 20a, 20b extending laterally over the integrated circuit elements 18a, 18b with a contact pad 66a, 66b, respectively, the contact pad 66a, 66b being provided on the respective circuit portion 62a, 62b. As shown in FIG. 4, the circuit portion 62a of the first detector 11a is laterally spaced from the integrated circuit element 18b of the second detector 11b. This enables a gap between the two adjacent integrated circuit elements 18a, 18b which allows to dispose an interconnection, such as the wire bond 64a.

Preferably, the wire bond 64a is configured to direct I/O and/or power signals between the integrated circuit element 18a and the substrate element 20a. The I/O signals are for instance digital control, data readout and/or analogue signals. The electric signals, in particular the pixel signals, which have been routed through the interposer element 16a are processed by the integrated circuit element 18a. Preferably, the processed pixel signals do not need to be routed out. The result of this processing can be read out via the I/O signals. The readout data is preferably used to form an image corresponding to the processed impinged photons.

Advantageously, the I/O and/or power signals are not directed through the interposer element 16a, 16b. In sensor devices known in the past, both the routing paths for pixel signals (shown in FIG. 2b) and the paths for directing the I/O and/or power signals are arranged within the interposer element. This means that the routing paths for pixel signals are capacitively coupled to the directing paths for the I/O and/or power signals. In the present sensor device 10, however, signal interferences, cross-talks and noise between the I/O and/or power signals on one hand and the pixel signals on the other hand are significantly reduced. This leads to higher signal integrity while enabling the four-sided tileability.

Figure 5:
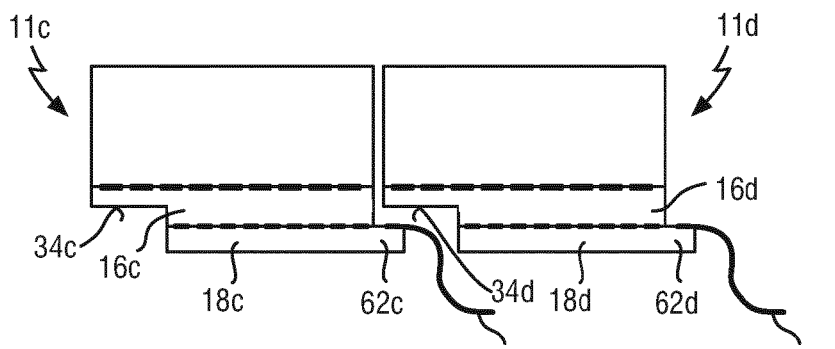
FIG. 5 shows a schematic representation of two adjacent detectors according to another embodiment.

FIG. 5 shows an alternative embodiment to that of FIG. 4. The detectors 11c, 11d are essentially the same as those shown in FIG. 4, except that the substrate element 20a, 20b is replaced by a flexible substrate 68c, 68d. The flexible substrates 68c, 68d are electrically connected with the corresponding circuit section 62c, 62d of the first and the second detectors 11c, 10d, preferably each via a contact pad. In a preferable embodiment, the flexible substrates 68c, 68d comprise each a direct flip-chip and/or a printed circuit board (PCB).

In all embodiments shown above, the extrusion 32 of the interposer element 16, 16', 16a-16d may be realized by etching, in particular chemical etching, grinding and/or mechanical milling. Alternatively, the extrusion 32 may be formed during the manufacturing of the interposer element 16, 16', 16a-16d. One or more components of the individual detector 11 comprise preferably a rectangular, in particular squared cross-section with respect to a surface normal perpendicular to the front surface 24, while a hexagonal or circular cross-section may be realized.

Figure 6:
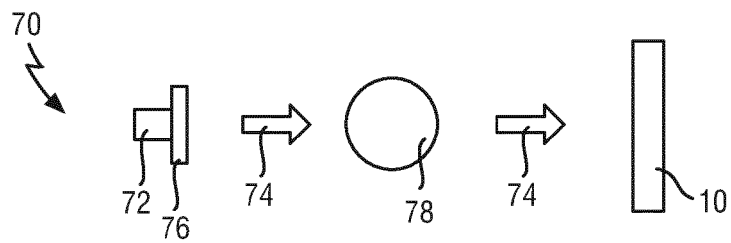
FIG. 6 shows a schematic representation of an imaging system according to an embodiment.

FIG. 6 shows a schematic representation of an imaging system 70 for detecting radiation signals of a subject 78, comprising a radiation source 72 for generating a plurality of radiation signals 74, radiation directing means 76 for directing the generated radiation signals 74, in particular photons, to a subject 78, and a sensor device 10 for detecting directed radiation signals 74 transmitted through the subject 78. The radiation source 72 may be preferably a point source. The sensor device 10 may be in accordance with one of the afore-mentioned embodiments in FIGS. 1-5. The sensor device 10 is disposed on opposite side of the radiation source 72 and the radiation directing means 76 with respect to the subject 78 (for example, a patient).

Figure 7:
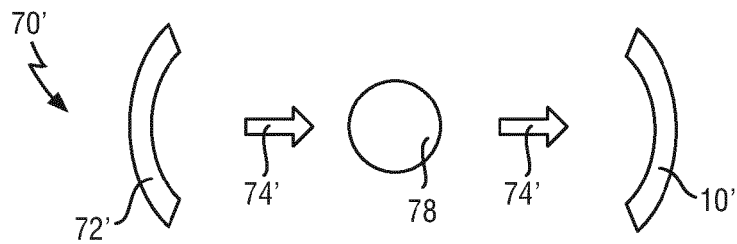
FIG. 7 shows a schematic representation of an imaging system according to another embodiment.

Preferably, the sensor device 10 comprises an array of detectors 11 which are aligned linearly. Alternatively, as shown in the imaging system 70' in accordance with another embodiment in FIG. 7, the sensor device 10' comprises an array of detectors 11 which are aligned to form a curvature. Further preferably, the radiation source 72' of the imaging system 70' in FIG. 7 comprises an internal radiation directing means, wherein the radiation source 72' is also formed with a curvature. For instance, the radiation source 72' comprises a plurality of individual point sources arranged in a curved surface. Preferably, the radiation source 72' and the sensor device 10' are arranged on a ring and are rotatable around an axis so that the radiation signals 74' may impinge the subject 78 in various directions. It is understood that the radiation source 72 and/or the sensor device 10 in the imaging system 70 of FIG. 6 may also be rotatable around an axis. In addition, the sensor device 10 in FIG. 6 may also comprise a curved array of detectors 11 as shown in FIG. 7.

The imaging systems 70, 70' may be a CT imaging system, preferably a Spectral CT imaging system. To this end, the radiation sources 72, 72' are configured to emit X-rays using one or more of the methods known in the field, such as thermionic and/or solid-state electron emitters, tungsten filament, tungsten plate, field emitter, thermal field emitter, dispenser cathode, thermionic cathode, photo-emitter, and/or ferroelectric cathode. A system controller may be integrated to the imaging system 70, 70' which controls the power and/or signals of the imaging systems 70, 70'. One or more displays may also be integrated to display medical images generated using the imaging system 70, 70'. A CT imaging system, in particular a Spectral CT imaging system, has an area coverage of typically 1000 mm×64 mm or more. For the four-sided tileability, the individual detectors 11 are arranged to form the sensor device 10, 10' in a mosaic manner.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A sensor device for detecting X-ray radiation signals, comprising
a sensor array comprising a plurality of detectors, the plurality of detectors include a first detector and a second detector adjacent to said first detector, wherein each detector comprising:
a receiver surface for receiving a plurality of radiation signals transmitted through or emanating from a subject;
a sensor element for converting said received plurality of radiation signals into a plurality of corresponding electric signals;
an interposer element extending laterally between a first side and a second side, said interposer element comprising a front surface facing said sensor element and a back surface parallel to said front surface, wherein said interposer element comprises a front contact arrangement on said front surface, a back contact arrangement on said back surface, and an extrusion comprising an extrusion surface;
wherein said front contact arrangement directs said plurality of electric signals to said back contact arrangement; and
an integrated circuit element facing said back surface and electrically connected to said back contact arrangement, said integrated circuit element comprising a circuit portion extending laterally over said back surface on said second side;
wherein said front surface extending laterally over said back surface on said first side by said extrusion, said circuit portion of said first detector overlapping vertically with and being vertically spaced from said extrusion surface of said second detector.

2. The sensor device according to claim 1, wherein said extrusion surface is arranged between said front surface and said back surface.

3. The sensor device according to claim 1, wherein said extrusion surface comprises a surface portion parallel to said front surface.

4. The sensor device according to claim 1, wherein said first side of said interposer element comprises an upper side surface connecting said front surface with said extrusion surface, and/or a lower side surface connecting said back surface with said extrusion surface, at least one of said upper side surface and said lower side surface 828*b*) being perpendicular to said front surface.

5. The sensor device according to claim 1, wherein said second side of said interposer element is perpendicular to said front surface.

6. The sensor device according to claim 1, wherein said each detector further comprises a substrate element electrically connected to said circuit portion.

7. The sensor device according to claim 6, wherein said substrate element is configured to extend laterally over said circuit portion.

8. The sensor device according to claim 6, wherein said circuit portion comprises a contact pad and a wire bond, wherein said substrate element is electrically connected to said contact pad by said wire bond.

9. The sensor device according to claim 1, wherein said each detector further comprises a flexible substrate.

10. The sensor device according to claim 1, wherein said integrated circuit element of said first detector is laterally spaced from said integrated circuit element of said second detector.

11. The sensor device according to claim 1, wherein said front contact arrangement comprises a plurality of front contact pads, wherein said back contact arrangement comprises a plurality of back contact pads, wherein each of said plurality of front contact pads is configured to direct one of said plurality of electric signals to a corresponding one of said plurality of back contact pads.

12. The sensor device according to claim 11, wherein each of said plurality of front contact pads is provided with a first lateral dimension and each of said plurality of back contact pads is provided with a second lateral dimension, said first lateral dimension being larger than said second lateral dimension.

13. The sensor device according to claim 11, wherein a quantity of said plurality of front contact pads the same as a quantity of said plurality of back contact pads.

14. The sensor device according to claim 1, wherein said interposer element is formed using pressed polyamide layers.

15. An imaging system for detecting radiation signals, comprising:
   a radiation source for generating a plurality of radiation signals;
   radiation directing means for directing said generated plurality of radiation signals to a subject; and
   a sensor device as claimed in claim 1 for detecting said directed plurality of radiation signals.

* * * * *